(12) United States Patent
Sevenster (10) Patent No.: US 10,930,379 B2
(45) Date of Patent: Feb. 23, 2021

(54) SYSTEM FOR MAPPING FINDINGS TO PERTINENT ECHOCARDIOGRAM LOOPS

(71) Applicant: KONINKLIJKE PHILIPS N.V., Eindhoven (NL)

(72) Inventor: Merlijn Sevenster, Haarlem (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 111 days.

(21) Appl. No.: 15/762,105

(22) PCT Filed: Oct. 3, 2016

(86) PCT No.: PCT/IB2016/055907
§ 371 (c)(1),
(2) Date: Mar. 22, 2018

(87) PCT Pub. No.: WO2017/056078
PCT Pub. Date: Apr. 6, 2017

(65) Prior Publication Data
US 2018/0286503 A1    Oct. 4, 2018

Related U.S. Application Data

(60) Provisional application No. 62/289,516, filed on Feb. 1, 2016, provisional application No. 62/236,358, filed on Oct. 2, 2015.

(51) Int. Cl.
*G16H 15/00*    (2018.01)
*G06F 19/00*    (2018.01)
(Continued)

(52) U.S. Cl.
CPC ............ *G16H 15/00* (2018.01); *A61B 5/044* (2013.01); *G06F 19/00* (2013.01); *G06F 19/321* (2013.01); *G16H 30/20* (2018.01); *G16H 50/70* (2018.01)

(58) Field of Classification Search
CPC .... G06F 1/00–2221/2153; G16H 10/00–80/00
See application file for complete search history.

(56) References Cited

U.S. PATENT DOCUMENTS 5,911,133 A  *  6/1999  Soble ..................... A61B 8/00
                                                    600/440
5,987,345 A  * 11/1999  Engelmann .......... G06F 19/321
                                                    600/407
(Continued)

FOREIGN PATENT DOCUMENTS

WO     2014155273 A1   10/2014
WO     2015092633 A1    6/2015

OTHER PUBLICATIONS

Koninklijke Philips Electronics N. V., "Advanced viewing and workflow—Philips IntelliSpace PACS Radiology 4.4 diagnostic reading solution," Aug. 2011.*

*Primary Examiner* — Elaine Gort
*Assistant Examiner* — Jonathon A. Szumny (57) ABSTRACT

Echocardiogram reporting uses a list of standard echocardiogram findings (20) and a standard echocardiogram finding-relevant echocardiogram view lookup table (22). An echocardiogram reporting workstation (10) comprises a display component (12) and at least one user input component (14, 16, 18), and performs an echocardiogram examination reporting method including: interfacing with a user to enable the user to enter a current report (30) on a current echocardiogram examination of a cardiac subject; detecting a current finding value for a standard echocardiogram finding in the current report; and detecting a prior finding value for the echocardiogram finding in a prior report (36) on a prior echocardiogram examination of the cardiac subject. If a change between the current finding value and the prior finding value satisfies a significance criterion (44), a relevant change panel (52) simultaneously displays current and prior (Continued)

echocardiogram loops for a relevant echocardiogram view relevant to the echocardiogram finding.

19 Claims, 4 Drawing Sheets

(51) Int. Cl.
    *G16H 30/20*     (2018.01)
    *G16H 50/70*     (2018.01)
    *A61B 5/044*     (2006.01)

(56) References Cited

U.S. PATENT DOCUMENTS

| | | | | |
|---|---|---|---|---|
| 6,629,937 | B2 * | 10/2003 | Watrous | A61B 7/00 128/920 |
| 7,822,627 | B2 * | 10/2010 | St. Martin | G16H 15/00 705/3 |
| 8,170,303 | B2 | 5/2012 | Zhou et al. | |
| 8,560,968 | B1 * | 10/2013 | Nair | G16H 40/63 715/839 |
| 9,378,331 | B2 * | 6/2016 | Reicher | G06F 19/321 |
| 10,130,332 | B2 * | 11/2018 | Kim | A61B 8/0883 |
| 10,376,239 | B2 * | 8/2019 | Park | A61B 8/465 |
| 2002/0024530 | A1 * | 2/2002 | Van Liere | G06F 3/04845 715/700 |
| 2004/0008028 | A1 * | 1/2004 | Horger | A61B 5/055 324/306 |
| 2007/0064987 | A1 | 3/2007 | Esham et al. | |
| 2007/0106633 | A1 * | 5/2007 | Reiner | G06Q 10/06 |
| 2007/0127795 | A1 | 6/2007 | Lau et al. | |
| 2008/0071174 | A1 * | 3/2008 | Waki | A61B 8/08 600/442 |
| 2008/0154928 | A1 * | 6/2008 | Bashyam | H03M 7/30 |
| 2008/0250070 | A1 * | 10/2008 | Abdulla | G16H 40/63 |
| 2009/0132588 | A1 * | 5/2009 | Mahesh | G06Q 10/00 |
| 2009/0149749 | A1 * | 6/2009 | Heron | A61B 8/08 600/437 |
| 2009/0171225 | A1 * | 7/2009 | Gadodia | G16H 15/00 600/508 |
| 2009/0185732 | A1 * | 7/2009 | Zhang | G06F 19/321 382/132 |
| 2010/0191541 | A1 * | 7/2010 | Prokoski | A61B 5/0064 705/2 |
| 2010/0260399 | A1 * | 10/2010 | Hajnal | G06F 19/321 382/131 |
| 2011/0002515 | A1 | 1/2011 | Futami et al. | |
| 2011/0137175 | A1 * | 6/2011 | Hossack | A61B 8/085 600/454 |
| 2012/0096524 | A1 * | 4/2012 | Kovalan | G06F 19/321 726/5 |
| 2012/0130223 | A1 | 5/2012 | Reicher | |
| 2012/0278105 | A1 * | 11/2012 | Luszcz | G06F 19/321 705/3 |
| 2013/0011027 | A1 | 1/2013 | Zillner | |
| 2013/0216112 | A1 | 8/2013 | Graessner | |
| 2014/0006926 | A1 * | 1/2014 | Yeluri | G16H 15/00 715/234 |
| 2014/0031688 | A1 * | 1/2014 | Perrey | A61B 8/5276 600/443 |
| 2014/0149407 | A1 * | 5/2014 | Qian | G06F 19/321 707/737 |
| 2014/0204242 | A1 * | 7/2014 | Anderson | G06F 19/321 348/231.5 |
| 2015/0269745 | A1 * | 9/2015 | Klimer | G06T 7/194 382/103 |
| 2016/0085725 | A1 * | 3/2016 | Leonard | G06K 9/6272 702/189 |
| 2016/0125171 | A1 * | 5/2016 | Finken | G06Q 10/10 705/2 |
| 2016/0128673 | A1 * | 5/2016 | Lee | A61B 8/463 600/441 |
| 2018/0289354 | A1 * | 10/2018 | Cvijanovic | A61B 8/08 |

* cited by examiner

SYSTEM FOR MAPPING FINDINGS TO PERTINENT ECHOCARDIOGRAM LOOPS

CROSS-REFERENCE TO PRIOR APPLICATIONS

This application is the U.S. National Phase application under 35 U.S.C. § 371 of International Application No. PCT/IB2016/055907, filed on Oct. 3, 2016, which claims the benefit of U.S. Patent Application No. 62/289,516, filed on Feb. 1, 2016 and U.S. Patent Application No. 62/236,358 filed on Oct. 2, 2015. These applications are hereby incorporated by reference herein.

FIELD

The following relates generally to the echocardiography arts, echocardiography workstation arts, related information technology arts, and the like.

BACKGROUND

Echocardiograms are ultrasound echoes of the heart acquired for the purpose of cardiology examination. In a typical echocardiogram examination the heart is imaged in one or more standard views, with a "movie" sequence called a "loop" acquired in each view. Standard echocardiogram views include: the peristernal long axis (PLAX) view; the peristernal short axis (PSAX) view; the apical 4 chamber (AP4) view; the apical 2 chamber (AP2) view; the apical 3 chamber (AP3) view; and the subcostal (SC) view. The sequence of images making up each loop is typically stored as a single file or data structure in an echocardiography information technology (IT) system. Each view is a large data structure (e.g. gigabytes/view in some cases) since it is made up of an extended sequence of images. Consequently, it is common for the echocardiograph IT system to employ an archival server for storing the echocardiogram views of older examinations.

Echocardiography is a highly specialized clinical area, and an echocardiography examination is usually performed and read by a specialist, known as an echocardiologist, rather than by a general-practice radiology technician or radiologist. Particular findings are most easily made on the basis of specific views, and the echocardiologist writes up the report after reviewing the relevant views. For some types of examination, practice guidelines call for comparing the current findings with those of the most recent prior echocardiography examination (if any). For example, the American Society of Echocardiography (JASE 24, 1-10) recommends the following with respect to exam comparison: "a comparison with the images from at least the most recent prior study should be performed to highlight findings that are new, unchanged, or progressive. The details of this comparison must be provided in the summary or conclusion section." This comparison can be a difficult part of the examination reading process. The echocardiologist must compare the current and prior reports to identify corresponding findings. When a finding calling for comparison is identified, the echocardiologist then reviews grids of thumbnail images for the loops of the current and prior examinations, and identifies and retrieves the appropriate view loops in each examination for detailed side-by-side or left-right visual comparison. This retrieval process may require accessing the archival server for the past examination view loop(s), which can introduce substantial delay since the (possibly gigabytes-sized) view file or data structure must be downloaded over the hospital information system (HIS) network or other electronic data network. At the echocardiography reading workstation, the echocardiologist pages back and forth between the current report window, the prior report window, and the retrieved views window in order to compare the findings, then returns to the current report window in order to write up a natural language exposition of the findings comparison. While some echocardiography workstation systems provide finding codes (FCs) for expedited entry of findings, the large number of possible current/past examination finding comparisons has generally led to such workstations not including FCs for finding comparisons.

In view of the foregoing difficulties, the recommended comparison with the most recent prior examination is sometimes omitted. However, omitting this recommended comparison can result in failure to capture clinically important information about the progression or regression of identified cardiac pathologies. Even when considering the current examination alone, existing echocardiography workstation and IT systems do not provide efficient mechanisms for linking findings with relevant echocardiographic views.

The following discloses a new and improved systems and methods that address the above referenced issues, and others.

SUMMARY

In one disclosed aspect, an echocardiogram reporting workstation comprises a display component, at least one user input component, a non-transitory storage medium storing a list of standard echocardiogram findings and a standard echocardiogram finding-relevant echocardiogram view lookup table, and an electronic data processing component programmed to perform an echocardiogram examination reporting method including: interfacing with a user via the display component and the at least one user input component to enable the user to enter a current report on a current echocardiogram examination of a cardiac subject; during the interfacing, detecting a current finding value for an instant standard echocardiogram finding of the list of standard echocardiogram findings in the current report; in response to a change between the current finding value and a prior finding value for the instant standard echocardiogram finding in a prior report on a prior echocardiogram examination of the cardiac subject satisfying a significance criterion, displaying a notification of the change on the display component; and in response to user selection of the notification via the at least one user input component, simultaneously displaying echocardiogram loops of the current echocardiogram examination and the prior echocardiogram examination for a relevant echocardiogram view that is relevant to the instant standard echocardiogram finding according to the standard echocardiogram finding relevant echocardiogram view lookup table.

In another disclosed aspect, a non-transitory storage medium stores a list of standard echocardiogram findings, a standard echocardiogram finding-relevant echocardiogram view lookup table, and instructions executable by an echocardiogram reporting workstation comprising a display component and at least one user input component to perform an echocardiogram examination reporting method including: interfacing with a user via the display component and the at least one user input component to enable the user to enter a current report on a current echocardiogram examination of a cardiac subject; detecting a current finding value for an instant standard echocardiogram finding of the list of standard echocardiogram findings in the current report;

detecting a prior finding value for the instant standard echocardiogram finding in a prior report on a prior echocardiogram examination of the cardiac subject; and conditional at least upon a change between the current finding value and the prior finding value satisfying a significance criterion, simultaneously displaying echocardiogram loops of the current echocardiogram examination and the prior echocardiogram examination for a relevant echocardiogram view that is relevant to the instant standard echocardiogram finding according to the standard echocardiogram finding relevant echocardiogram view lookup table.

In another disclosed aspect, an echocardiogram reporting method is performed using a workstation including a display component and at least one user input component. The echocardiogram reporting method comprises: interfacing with a user via the workstation to enable the user to enter a current report on a current echocardiogram examination of a cardiac subject; detecting a current finding value in the current report for an echocardiogram finding; determining a change between the current finding value and a prior finding value for the echocardiogram finding in a prior report on a prior echocardiogram examination of the cardiac subject; displaying a notification of the change on the display component of the workstation in response to the change satisfying a significance criterion; and simultaneously displaying echocardiogram loops of the current echocardiogram examination and the prior echocardiogram examination for a relevant echocardiogram view that is relevant to the echocardiogram finding in response to user selection of the notification via the at least one user input component of the workstation.

One advantage resides in providing an improved echocardiography workstation and IT system with reduced view file or data structure retrieval delays.

Another advantage resides in providing an improved echocardiography workstation and IT system which facilitates comparing findings of a current examination with corresponding findings of a most recent prior echocardiography examination.

Another advantage resides in providing an improved echocardiography workstation and IT system which links findings with relevant echocardiographic views.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Figure 1:
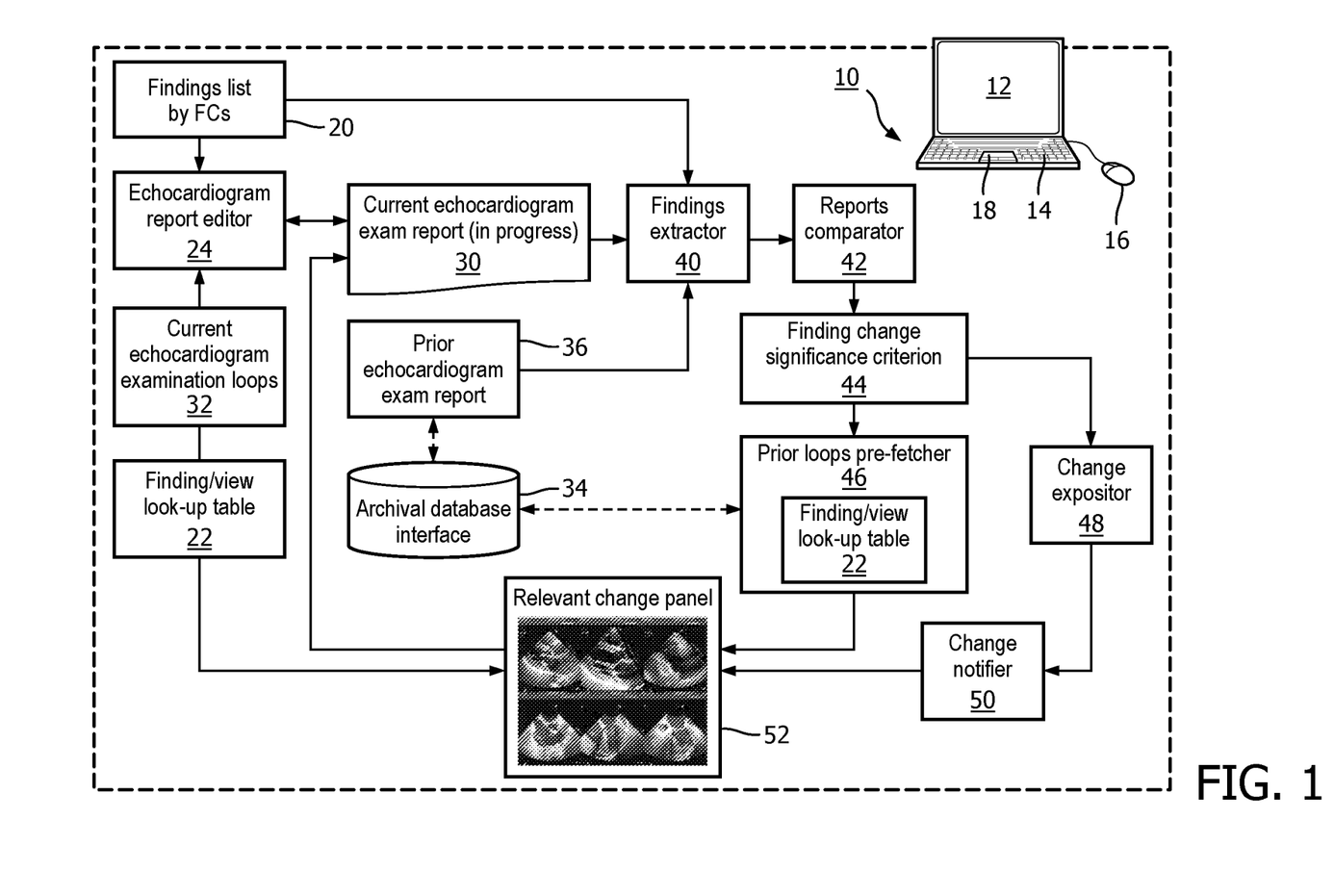
FIG. 1 diagrammatically shows an echocardiogram reporting workstation configured to perform an echocardiogram examination reporting method including automated or semi-automated comparison of current report findings with findings of a prior report.

With reference to FIG. 1, an echocardiogram reporting workstation 10 includes a display component 12 (e.g., an LCD display, plasma display, OLED display, or so forth, preferably being a high resolution color display; the illustrative display component 12 includes a single screen but optionally the display component may include two or more screens) and at least one user input component (e.g., an illustrative keyboard 14, mouse 16, trackpad 18, or other pointing device, touch-sensitive overlay of the display 12, and/or so forth). Although not specifically illustrated, it is understood that the workstation 10 includes an electronic data processing component, such as a microprocessor (which may be multi-core and/or may include multiple processors and ancillary components such as RAM, an optional math co-processor, ALU, and/or other ancillary electronics, or so forth. While the illustrative echocardiogram reporting workstation 10 is a unitary computer, it will be further understood that the processing power of the workstation may be variously distributed, e.g. the electronic data processing component may comprise a remote server computer accessed via a local area network and/or the Internet by a network terminal having the display component 12 and user input component(s) 14, 16, 18.

The disclosed echocardiogram examination reporting (and report reading) methods may also be embodied as a non-transitory storage medium storing instructions readable and executable by the workstation 10 (or by an examination report reading station, e.g. see FIG. 4) such as a hard disk drive or other magnetic storage medium, and/or an optical disk or other optical storage medium, and/or a flash memory or other electronic storage medium, various combinations thereof, or so forth. As will be discussed, the non-transitory storage medium may further store relevant data structures such as a standard echocardiogram findings list 20 and a standard echocardiogram finding-relevant echocardiogram view lookup table 22. These data structures 20, 22 may be stored on the same non-transitory storage medium that stores the readable/executable instructions, or may be stored on different non-transitory storage media. (Note that for ease of illustration two instances of the finding-view lookup table 22 are shown in FIG. 1, but they represent the same finding-view lookup table 22.

The findings list 20 stores standard echocardiogram examination findings. Advantageously, echocardiology is a relatively well-established field for which finite standard set of findings can be constructed and represented in the list 20 (where "list" is to be understood as encompassing any data structure storing relevant information about the standard findings, e.g. the list may be a table, spreadsheet, ASCII text list, or so forth). The standard set of findings 20 may be updated occasionally to reflect current state of the art in echocardiology, additional findings made feasible by acquisition of newer ultrasound equipment, or so forth. A non-exhaustive list of standard findings that an echocardiologist may be expected to address in a typical echocardiology examination may include one or more of: left ventricular function; right ventricular function; mitral regurgitation; tricuspid regurgitation (TR); aortic regurgitation; pericardial effusion; and/or so forth. Each finding may be represented in various ways, such as by textual keywords, or a finding code, a combination thereof, or so forth. The findings list 20 optionally includes other information such as finding data type (e.g., scale value, binary value, measurement) and optionally a range of allowable values for the finding. The standard findings may be those promulgated by a professional organization such as the American Society of Echocardiology, optionally augmented by additional site-specific findings or site-specific finding modifications (e.g. hospital-specific). Alternatively, the standard findings may be defined for a particular installation or a particular hospital.

The standard echocardiogram finding-relevant echocardiogram view lookup table 22 stores a relevant view for each standard finding. This data structure embodies the knowledge in the echocardiology arts that standard views are typically acquired in an echocardiology examination. For example, common views include: the peristernal long axis (PLAX) view; the peristernal short axis (PSAX) view; the apical 4 chamber (AP4) view; the apical 2 chamber (AP2) view; the apical 3 chamber (AP3) view; and the subcostal (SC) view. Each echocardiogram loop is typically acquired for one such standard view (although the echocardiologist may choose to acquire other, non-standard views). Echocardiology guidelines have identified one or more relevant views that are optimal for making each finding, and these are tabulated in the finding-view lookup table 22. As with the findings list 20, the finding-view lookup table 22 is to be understood as encompassing any data structure capable of storing the information linking a standard finding with one or more relevant views, e.g. the finding-view lookup table 22 can be a list, spreadsheet, relational database table, or so forth. Table 1 presents one illustrative finding-view lookup table 22.

TABLE 1 illustrative finding-view lookup table

| Standard Finding | Relevant view(s) |
| --- | --- |
| left ventricular function | PLAX, SLAX, AP4, AP2 |
| right ventricular function | PLAX, SLAX, AP4, AP2 |
| mitral regurgitation | PLAX color, AP4 color, AP2 color |
| tricuspid regurgitation (TR) | PLAX color, AP4 color, AP2 color |
| aortic regurgitation | PLAX |
| pericardial effusion | SC |

Again, as with the findings list 20, the relatively mature state of echocardiology enables the findings-view lookup table 22 to be constructed as a finite data structure.

With continuing reference to FIG. 1, the workstation 10 implements an echocardiogram report editor 24 that interfaces a user (typically an echocardiologist) via the display component 12 and the at least one user input component 14, 16, 18 to enable the user to enter a current report 30 (i.e., an in-progress report 30) on a current echocardiogram examination of a cardiac subject. The current report 30 reports the user's findings on the current echocardiogram examination represented by stored (current) echocardiogram examination loops 32. The echocardiogram report editor 24 may, by way of non-limiting illustrative example, be the Xcelera integrated multi-modality image management system for cardiovascular information (available from Koninklijke Philips N.V., Eindhoven, the Netherlands) modified to incorporate automated comparisons with a prior examination report as disclosed herein. In general, the echocardiogram report editor 24 provides features such as a text editing panel for entering report text, image viewing panels for viewing echocardiogram loops viewing individual frames of a loop, for measuring dimensions, or so forth, graphical user interface (GUI) dialogs for performing various operations, and et cetera. In some embodiments (including Xcelera), the user may enter a finding by way of entering a finding code (FC), in which case the standard findings list 20 is preferably indexed by FC. The echocardiogram report editor 24 preferably also provides a GUI mechanism for selecting an echocardiogram loop or loops for viewing in a viewing panel for example, a grid of loop thumbnail images are displayed, with each loop represented by a thumbnail, for example generated as a reduced-size version of a first frame of the loop. The user may then click on a thumbnail with the mouse 16, or otherwise select a thumbnail, which is then brought up in a separate viewing panel. Preferably the viewing panel enables viewing of multiple loops simultaneously, e.g. side-by-side or above-below.

In embodiments disclosed herein, the workstation 10 provides an integrated and automated prior examination comparison tool. In some echocardiology information technology (IT) architectures, due to the large size of echocardiogram loops (e.g. gigabytes/view in some cases) older examination data are stored in a high-capacity archival database, and the workstation 10 includes an archival database interface 34 for accessing these older examinations. For example, the archival database interface 34 may comprise a hospital IT network connection to a Picture Archiving and Communication System (PACS, not shown) that stores the older echocardiogram data. When the user initiates editing of the current report 30 on the current echocardiogram examination of the cardiac subject, the user is required to enter patient identification (ID) information (e.g. a patient ID, medical ID, social security number, or so forth). The workstation 10 searches the archival database for any prior echocardiogram examination on this cardiac subject. If none is found, then there is no need to compare the current findings with any (non-existent) prior examination. On the other hand, if the workstation 10 finds one or more prior echocardiogram examinations on the cardiac subject, then it identifies the most recent prior echocardiogram examination and retrieves a prior echocardiogram examination report 36 on the (most recent) prior echocardiogram examination of the cardiac subject in order to perform automated checking of finding values of the current report 30 against finding values of the prior report 36.

To this end, the electronic data processing component of the workstation 10 is programmed to implement the following modules. A findings extractor 40 detects finding values for standard findings (as defined in the findings list 20) in the current report 30 and in the prior report 36. For each finding value for a standard finding of the current report 30, a reports comparator 42 searches the prior report 36 to identify a prior finding value for the same (i.e. the instant) standard finding. The change between the current and prior finding values is compared against a finding change significance criterion (typically a threshold). If the change does not satisfy the significance criterion then it is ignored. (In some embodiments, if the comparison with the prior finding value should be discussed in the current report 30 even if there is no change or only a small change, then the significance criterion can be set to always identify the change as significant, even if there is no change at all). If the change is deemed significant, then the prior findings comparison tool performs two operations: a pre-fetcher 46 retrieves loop(s) of the prior examination showing a relevant view (as indicated by the findings-loops lookup table 22) from the archival database; and a change expositor 48 generates a natural language exposition of the change.

The pre-fetcher 46 improves workflow efficiency by pre-fetching the relevant prior echocardiogram loops (again, this may be gigabytes of data for each loop) as soon as the components 40, 42, 44 recognize that these loops may indeed be relevant. The retrieved prior loops may, for example, be stored on a local hard disk, solid state drive (SSD), or other local storage of the workstation 10. In this way, if and when the user selects to compare the relevant current and prior loops to assess a particular finding change, the user does not experience a potential delay for retrieving the prior loops.

The change expositor 48 improves workflow efficiency by generating one or more proposed natural language expositions of the change, which can be automatically inserted into the current report 30 upon assent by the user. The change expositor 48 improves efficiency by reducing the need for the user to manually type an exposition of the change. For example, the change expositor 48 can use a natural language template for stating the change, with a fillable field for the value of the change.

A change notifier 50 notifies the user of the detected significant change in the instant standard finding. This notification may, for example, be a pop-up window, or may be listed in a notifications panel of the GUI interface provided by the report editor 24. If the user selects to review the change, then a relevant change viewing panel 52 is displayed which simultaneously displays current and prior echocardiogram loops, e.g. in an above-below arrangement in the illustrative example of FIG. 1. As diagrammatically shown in FIG. 1, the workstation 10 obtains the current loops from the local current loops storage (represented by block 32), and obtains the pre-fetched prior loops from a local storage populated by the prior loops pre-fetcher 46. The relevant change viewing panel 52 may also display the one or more proposed expositions of the change generated by the change expositor 48. If the user selects a change exposition for inclusion in the current report 30, then the selected exposition is automatically copied into the current report 30.

In the following, some suitable implementations of various components of the echocardiogram examination reporting workstation of FIG. 1 are described.

The findings extractor 40 can use a natural language analysis to detect finding values for standard findings. In a suitable approach, a text segment (e.g. paragraph) of free-form report text is processed to detect sentences (e.g., based on period/space locations) which are then scrutinized to detect findings using keywords defined in an echocardiography ontology such as MetaMap. For example, each standard finding may be listed as including associated keywords in the findings list 20, along with allowable values for the finding value of that standard finding. Alternatively, if the report editor 24 allows entry of finding values using finding codes (FCs), then the findings extractor 40 can detect a FC indicating a standard echocardiogram finding in the current report 30, and can detect the same FC in the prior report 36. The FC may be stored as ASCII text in the report and detected by matching the FC pattern, or if the report is more structured the FCs may be stored in the report as numeric fields or other structured data fields. Operation of the findings extractor 40 is facilitated by the finite universe of possible standard findings defined by the findings list 20 for the specific field of echocardiography.

To implement the prior loops pre-fetcher 46 and to enable the relevant change panel 52 to be populated with loops showing a view that is relevant for the instant standard finding, two steps need to be performed. First, the relevant view for the instant standard finding needs to be identified. This is done by referencing the standard echocardiogram finding-relevant echocardiogram view lookup table 22. Second, loops presenting that relevant view must be identified in the set of current examination loops 32, and in the set of prior examination loops of the prior examination stored in the archival database. Various approaches can be used. If loops are labeled by view, then identifying loops of the relevant view amounts to reading the view identification metadata tagged to the stored loops.

On the other hand, if the loops are not labeled by view, then image processing is suitably performed on the loops themselves (or on individual frames of the loops) or on thumbnail images representing the loops (such thumbnails are typically automatically generated by the report editor 24 for use in displaying a grid of loop thumbnails to enable the user to navigate and select loops for viewing). Some suitable image processing approaches for labeling echocardiogram loops with standard view labels are described, for example, in Zhou et al., U.S. Pat. No. 8,170,303. A difficulty with the imaging processing approach for view labeling is that the certainty of the view label may be less than 100%. In one approach, a certainty distribution over the various views is generated for a given loop by the image processing, and the loop is labeled with the view having maximum certainty value, even if it does not equal 100%. Optionally, if the maximum certainty value does not exceed a pre-determined threshold, more than one view can be assigned to a single loop.

The view labeling of the current and prior echocardiogram loops may be performed at different times during the processing. In one approach, all loops of an examination are labeled by view when the examination is loaded for the first time. In another approach, each loop is processed and labeled by view at the time of loop acquisition and storage. In another approach, a loop is labeled by view only when that loop is fetched or retrieved for processing. This latter approach may result in delays for the user, depending on the efficiency of the view determination. In addition to labeling by view, loops may be labeled with other pertinent information such as whether it is a color loop, whether the loop has been zoomed, by image depth, or so forth.

With the loops labeled by view, the retrieval of loops that are relevant to a given finding amounts to accessing the findings-views lookup table 22 with the instant standard finding as input and retrieving the corresponding view(s), and locating those loops of the current and/or prior examination labeled with the relevant view.

The reports comparator 42 operates on the findings identified by the findings extractor 40. For each finding value detected in the current report 30, the detected finding values of the prior report 36 are searched to locate a prior finding value for the same (instant) standard finding. Different findings may be capable of assuming different types of values. Some examples are given below.

A scale finding is a finding that makes an observation with respect to a certain scale of severity, such as normal/mild/moderate/severe. For example, if an echocardiogram report states "Left ventricular performance is moderately reduced" then the standard finding is "left ventricular function" and the finding value is "moderately reduced" which may optionally be converted to some other format, e.g. "moderately reduced" may be mapped onto a scale of 1-to-5. In one approach, if the foregoing is a finding value detected in the current report 30, then the prior report 36 is searched for the identical description except (possibly) for a different severity keyword. For example, the prior report 36 may contain: "Left ventricular performance is mildly reduced" so that the prior finding value is "mildly reduced". To allow for some flexibility in the matching, fuzzy matching strategies may be employed, e.g. a match may be identified for "Left ventricular function is normal" (recognizing "function" and "performance" are synonymous in this context.

A binary finding makes an observation as a binary value, for example a feature is observed, or it is not. For example: "Mitral valve prolapse." In this case, the prior report 36 is searched for scale finding values that are identical in their description except possibly for a negation marker. To allow for some flexibility in the matching, fuzzy matching strategies may again be employed, e.g. "There is no ventricular septal defect visualized" matches "Membranous ventricular septal defect, restrictive". Again, a finite ontology commonly used for echocardiography facilitates such fuzzy matching. The elements that are different in the two binary finding values may be normalized with respect to a binary scale, e.g., present/absent, or I/O.

A measurement finding reports a measurement for some measureable parameter. For example: "Left ventricular ejection fraction by single plane (AP4) method of discs is <V>" where <V> is a filled in measurement value. In this case the prior report 36 is searched for the same or similar (in terms of fuzzy matching) text except for having a (possibly) different value filled in at the field <V>. The change is then the difference between the current and prior measurements.

The finding change significance criterion 44 for a measurement finding is typically a threshold, i.e. if the measurement change exceeds (or equals or exceeds) a threshold then it is a significant change. For a scale finding, any change along the scale is likely to be deemed significant. For example, For instance, for measurements FCs, a minimal difference of 20% may be used as a significant difference for the left ventricular ejection fraction; and a jump from "normal" to "moderate" or "severe", or from "mild" to "severe", or the other way around, may be used as a significant difference for the status of aortic stenosis. Since a binary finding can assume only one of two values, any change in the value of a binary finding is deemed significant.

As previously noted, in some embodiments and for some findings, a comparison of current/prior finding values should be included even if the current and prior finding values are the same. This situation may arise, for example, if it is clinically significant that the finding is not changing. In this case the change significance criterion can be set to "Yes", i.e. the change is always deemed significant (even if there is no change).

Another situation that could be encountered is that there prior report 36 may not report any value for a finding made in the current report 30. This can be handled in various ways, depending on the type of finding. In one approach, the change is defined as "new finding" and is automatically deemed significant. This is particularly likely to be appropriate in the case of the current report indicating a positive value for a binary finding when the prior report 36 did not mention this finding. In such a case, it may be reasonably assumed that the finding was not mentioned in the previous report because it was not observed, in which case this is effectively a change from a negative result (feature not observed in the prior examination) to a positive result (feature now observed in the current examination). It is noted that since the user has the opportunity to review the relevant loops by way of the relevant change panel 52, reporting this situation as significant is advantageous because it alerts the user entering the current report 30 that the relevant loops of the prior examination should be re-examined to see if the feature was indeed absent.

The change expositor 48 receives the change (deemed significant according to the criterion 44) and generates a natural language statement explicating the change. In a suitable approach, the exposition is a textual template with fillable fields that are filled in with the value of the change. For instance: "Visual inspection of the left ventricular ejection fraction shows significant deterioration (<C> %)", where <C> is a fillable field that is filled in with the change value. In another embodiment, fields for all changed aspects of the examination are included in one template sentence, again using a standard template: "Visual inspection of ________, ________, ________, and ________ shows significant change" where the blanks represent findings found by the findings extractor 40. It is contemplated to provide more than one proposed natural language statement explicating the change, for example using different natural language phraseology. For example, one proposed statement may only identify the change, while another proposed statement may identify the prior and current finding values with the change as a parenthetical value. This enables the user to choose how detailed the explanation should be.

The relevant change panel 52 can provide various types of functionality. The change panel 52 simultaneously displays current/prior loops showing a view relevant to an instant finding. In the panel 52, when the user has visually inspected the changes, the user can assent to include the natural language sentences generated by the change expositor 48 in the current report 30, e.g., by clicking a button. In another implementation, clicking the button will include the finding in one umbrella change statement, explicating all aspects of the study that have changed since the prior exam. In yet another implementation, when the changes have been visually inspected, a relevant change statement is included automatically in the report.

Figure 2:
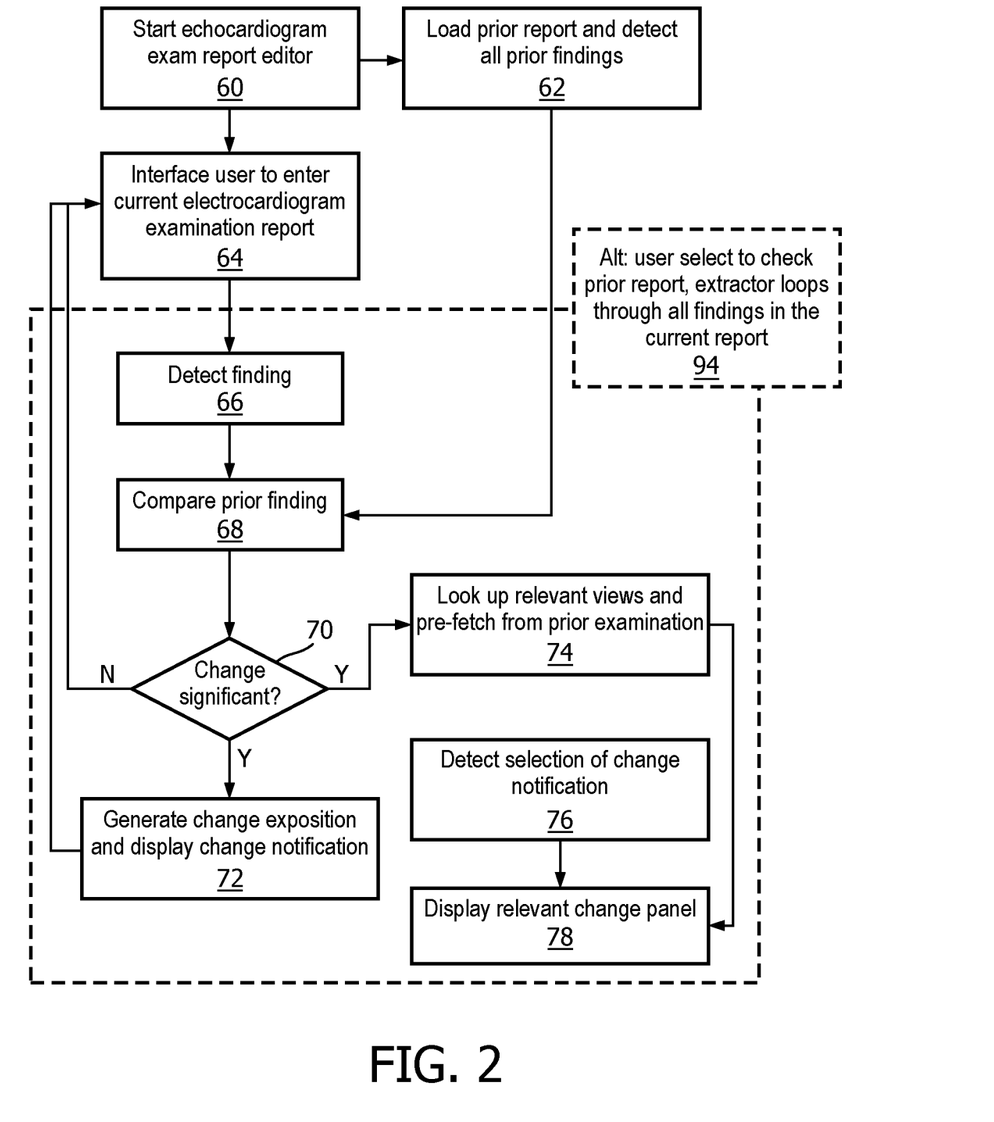
FIG. 2 diagrammatically shows illustrative embodiments of an echocardiogram examination reporting method suitably performed using the echocardiogram reporting workstation of FIG. 1.

With reference now to FIG. 2, some illustrative echocardiogram examination reporting methods suitably performed using the workstation 10 of FIG. 1 are described. Two embodiments are considered: a real-time comparison tool in which the current report 30 is continually processed as it is entered to detect a finding value immediately upon its entry into the current report 30; and a post-processing embodiment in which the user enters the complete current report 30 (except the section comparing with the prior report) and then selects to perform the prior report comparison (the post-processing embodiment is diagrammatically indicated in FIG. 2 using dashed lines).

Considering first the real-time comparison approach, the user starts the echocardiogram examination report editor 20 in an operation 60. In the illustrative example of FIG. 2, the startup 60 requires entry of the patient ID which is used in operation 62 to retrieve the prior report 36 and detect all prior findings in the prior report. (In this approach, the prior finding values in the prior report are detected before detecting the current finding values in the current report). In an operation 64 the user interfaces via the display component 12 and the at least one user input component 14, 16, 18 to enable the user to enter the current report 30 on a current echocardiogram examination of a cardiac subject. As this report entry proceeds, the newly entered report material analyzed in (near) real time by the findings extractor 40, and when the user enters a finding value it is thereby detected in an operation 66. In an operation 68, the change between the current finding value and the prior finding value from the prior report 36 is determined, and at a decision 70 the change is assessed using the significance criterion 44. If the change is not significant, then flow returns to the report entry operation 64 (or, alternatively, the various prior report comparison operations 66, 68, 70 are performed concurrently with the report entry 64).

On the other hand, if the decision 70 is that the change is significant, then in an operation 72 the change expositor 48 is invoked to generate one or more natural language expositions of the change and a notification of the change is provided to the user. In a concurrent operation 74 the prior loops pre-fetcher 46 consults the findings-view lookup table 22 to identify the view(s) relevant to the finding and the archival database interface 34 is accessed to retrieve the relevant prior loops. If the user selects the change notification generated in the operation 72, then in an operation 76 this selection is detected and in responsive operation 78 the relevant change panel 52 is displayed.

Figure 3:
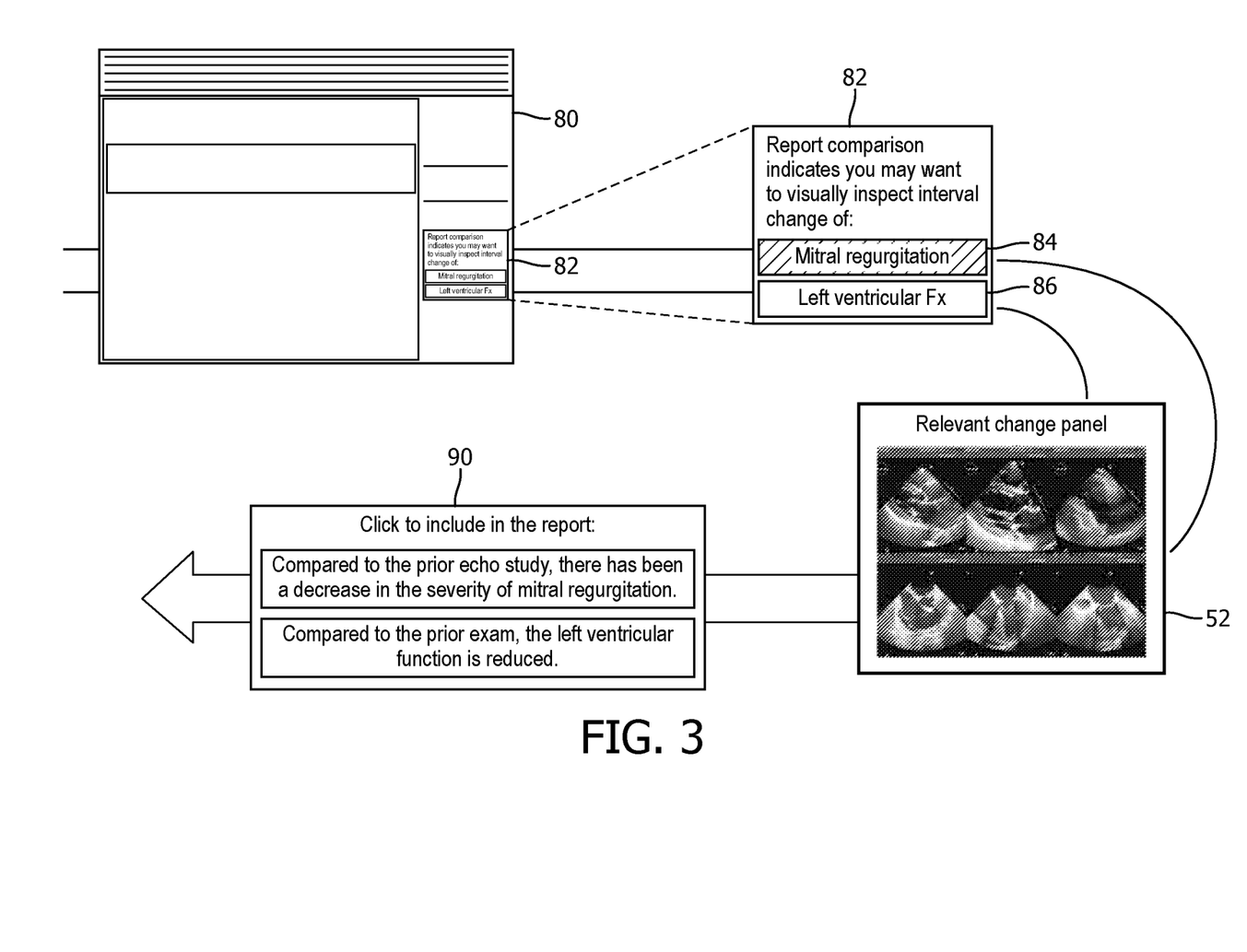
FIG. 3 diagrammatically shows illustrative embodiments of user display screenshots and user interfacing dialogs that may be suitably employed when performing an embodiment of the echocardiogram examination reporting method of FIG. 2 using the echocardiogram reporting workstation of FIG. 1.

With continuing reference to FIG. 2 and further reference to FIG. 3, illustrative suitable screenshots and GUI dialogs for this process are shown. A screenshot 80 may be shown on the display component 12 during the current report entry interfacing 64. A change notifications GUI dialog panel 82 presents notifications generated in the operation 72, such as is indicated in the screenshot 80 and shown in enlarged view to the right of the screenshot 80. The illustrative change notifications GUI dialog panel 82 provides the default header "Report comparison indicates you may want to visually inspect interval change of", and includes the generated notification 84 indicating change of mitral regurgitation and the generated notification 86 indicating change of left ventrical Fx. In the real-time monitoring embodiment, these notifications 84, 86 are generated in (near) real-time as the corresponding finding value is entered into the current report 30 in the operation 64; thus, if the user first entered the current value for mitral regurgitation this entry is detected in operation 66 and compared with the prior report in operations 68, 70, and when deemed to have a significant interval change versus the prior examination the notification 84 is displayed. Thereafter, the user continues to enter the current report 30 and in due course enters the finding value for left ventricular Fx which is detected in operation 66 and compared with the prior report in operations 68, 70, and when deemed to have a significant interval change versus the prior examination the notification 86 is displayed. Additional change notifications may continue to accumulate in the change notifications GUI dialog panel 82 as further findings are entered into the current report 30. At any time, the user can click on one of the change notifications 84, 86 in the illustrative example of FIG. 3, the user clicks on the mitral regurgitation interval change 84 (as indicated by shading of the notification 84) and this is detected in operation 76 causing the relevant change panel 52 to be brought up showing the current and prior loops for view(s) relevant to the mitral regurgitation finding. The relevant change panel 52 may also optionally show a GUI dialog 90 providing one or more proposed natural language expositions of the change: in the illustrative example two such expositions are proposed. If the user clicks on one of these proposed change expositions then the corresponding text is copied into the current report 30, where it will appear on the display 80.

With returning reference to FIG. 2, the foregoing embodiment employs real-time monitoring of newly entered report text by the findings extractor 40, so that whenever a new finding is entered it is immediately compared with the prior report 36 and, if a significant change is detected, the appropriate change notification is presented. In an alternative embodiment 94, indicated by dashed lines in FIG. 2, the findings extractor 40 does not continually monitor newly entered text. Rather, in this alternative embodiment the user enters the entire current report, except for the prior report comparison section. Then, the user selects to check the prior report 36, for example by clicking an appropriately labeled button (not shown) on the report entry display. Clicking this button triggers the prior report check, in which operations 66, 68, 70 and (for significant detected changes) operations 72, 74 are repeated for each detected finding value of the current report. The user will again be presented with a list of change notifications, but in this embodiment appearing substantially simultaneously upon selection of the "check prior report" button. The user can select any change notification which is detected 76 and processed 78 as already described.

The foregoing embodiments pertain to the echocardiography examination report entry phase. Relevant loop retrieval aspects of this system may also be advantageously leveraged during the echocardiography examination report reading phase, e.g. performed by the cardiologist who ordered the examination.

Figure 4:
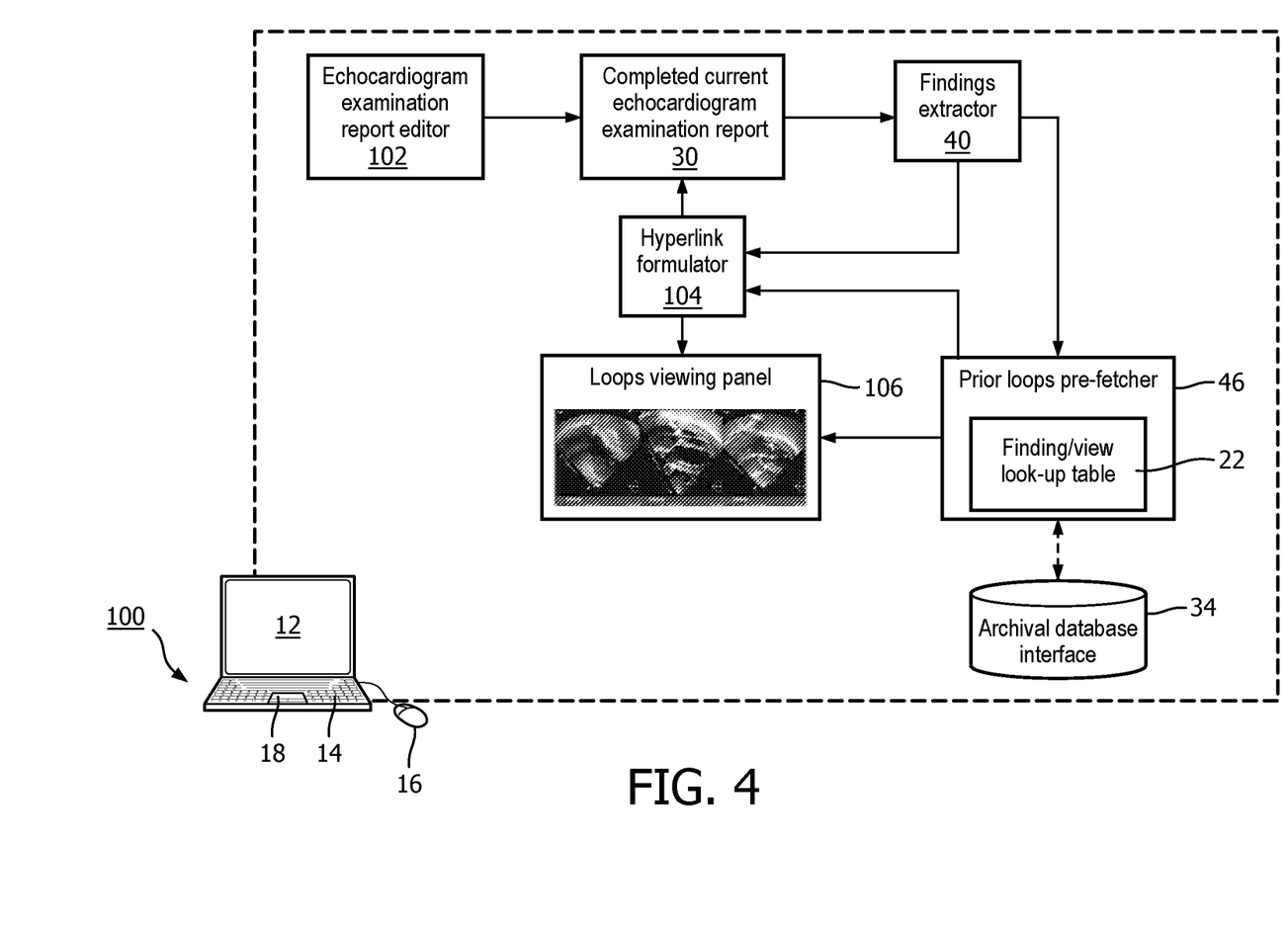
FIG. 4 diagrammatically shows an echocardiogram examination report reading workstation configured to perform an echocardiogram examination report reading method including hyperlinking findings in the report to echocardiogram loops that are relevant to the hyperlinking findings.

With reference now to FIG. 4, an echocardiogram report reading workstation 100 is implemented on the same hardware 12, 14, 16, 18 as the echocardiogram reporting workstation 10; however, it could alternatively be implemented on a different computer (e.g. on the cardiologist's office computer) from the reporting workstation 10. The echocardiogram report reading workstation 100 includes an electronic data processing component (e.g. microprocessor and ancillary electronics) to implement an echocardiogram report reader 102 which may, for example, provide a panel displaying the completed current echocardiogram examination report 30. The echocardiogram report reading workstation 100 is programmed to implement the findings extractor 40 which is applied to the completed current echocardiogram examination report 30 to identify finding values in the report 30. For each detected finding value, the prior loops pre-fetcher 46 looks up the relevant view(s) in the finding-view lookup table 22 and retrieves loops of the current examination showing the relevant view(s) via the archival database interface 34. (This assumes the current examination data including the loops have been offloaded to the archival database after completion of the current echocardiogram examination report 30). A hyperlink formulator 104 formats the text of each finding in the report 30 as a hyperlink, e.g. using conventional HTML-type markup tag of the form:

<a href="loop urls">finding text</a> where "loop urls" indicate file paths to the pre-fetched loops showing the relevant view(s), and finding text is the text of the finding in the completed current report 30. In this way, the user reading the current report 30 using the report reader 102 can click on the hyperlink of a finding value and a loops viewing panel 106 is displayed in response which displays the pre-fetched loops showing the relevant view(s) for the finding selected by clicking the hyperlink in the displayed report.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. An echocardiogram reporting workstation comprising:
a display component;
at least one user input component;
a non-transitory storage medium storing a list of standard echocardiogram findings and a standard echocardiogram finding-relevant echocardiogram view lookup table; and
an electronic data processing component programmed to perform an echocardiogram examination reporting method including:
interfacing with a user via the display component and the at least one user input component to enable the user to enter a current report on a current echocardiogram examination of a cardiac subject;
during the interfacing, detecting a current finding value for an instant standard echocardiogram finding of the list of standard echocardiogram findings in the current report;
in response to a change between the current finding value and a prior finding value for the instant standard echocardiogram finding in a prior report on a prior echocardiogram examination of the cardiac subject satisfying a significance criterion, displaying a notification of the change on the display component, identifying a relevant echocardiogram view according to the standard echocardiogram finding-relevant echocardiogram view lookup table, pre-fetching echocardiogram loop or loops of the prior echocardiogram examination images for the relevant echocardiogram view via an archival data storage interface, and storing the pre-fetched echocardiogram loop or loops of the prior echocardiogram examination images for the relevant echocardiogram view in storage; and
in response to a user selection of the notification via the at least one user input component, retrieving, via the user selection of the notification via the at least one user input component, the pre-fetched echocardiogram loop or loops of the prior echocardiogram examination images for the relevant echocardiogram view from the storage and then simultaneously displaying echocardiogram loops of the current echocardiogram examination images and the retrieved pre-fetched echocardiogram loop or loops of the prior echocardiogram examination images for the relevant echocardiogram view that is relevant to the instant standard echocardiogram finding according to the standard echocardiogram finding-relevant echocardiogram view lookup table.

2. The echocardiogram reporting workstation of claim 1 wherein the echocardiogram examination reporting method further includes:
generating a natural language exposition of the change;
displaying, on the display component, a proposal to include the natural language exposition of the change in the current report; and
responsive to receiving an assent to the proposal from the user via the at least one user input component, automatically incorporating the natural language exposition of the change into the current report.

3. The echocardiogram reporting workstation of claim 1 wherein the loops of images are labeled by view, further comprising identifying loops of images of the relevant view by reading view identification metadata tagged to the loops.

4. The echocardiogram reporting workstation of claim 1 wherein the list of standard echocardiogram findings is indexed by finding codes and the detecting of the current finding value in the current report comprises:
detecting a finding code for the instant standard echocardiogram finding in the current report.

5. The echocardiogram reporting workstation of claim 1 wherein the echocardiogram examination reporting method further includes:
detecting prior finding values for standard echocardiogram findings of the list of standard echocardiogram findings in the prior report;
wherein the detecting of the prior finding values is performed before detecting the current finding value.

6. The echocardiogram reporting workstation of claim 1 wherein the simultaneous displaying of echocardiogram loops of the current echocardiogram examination and the prior echocardiogram examination for the relevant echocardiogram view comprises:
performing image processing on at least one of the echocardiogram loops and thumbnail images representing the echocardiogram loops to assign view labels to the echocardiogram loops.

7. The echocardiogram reporting workstation of claim 1 wherein the echocardiogram examination reporting method further includes:
comparing the change between the current finding value and the prior finding value with a threshold;
wherein the change meets the significance criterion if it one of (i) equals or exceeds the threshold and (ii) exceeds the threshold.

8. The echocardiogram reporting workstation of claim 1 wherein the detecting of the current finding value in the current report during the interfacing includes monitoring the interfacing to detect the current finding value upon its entry by the user via the interfacing.

9. The echocardiogram reporting workstation of claim 1 wherein the detecting of the current finding value in the current report during the interfacing includes:
receiving a user selection to check the prior report via the at least one user input component; and
repeating the detecting to detect all current finding values for standard echocardiogram findings of the list of standard echocardiogram findings in the current report.

10. The echocardiogram reporting workstation of claim 1 wherein the electronic data processing component is further programmed to perform an echocardiogram report reading method including:
detecting finding values for standard echocardiogram findings of the list of standard echocardiogram findings in the current report;
displaying the current report with the detected findings being hyperlinked;
responsive to user selection of a hyperlink of a detected finding, identifying an echocardiogram view relevant to the selected detected finding according to the standard echocardiogram finding-relevant echocardiogram view lookup table and displaying the echocardiogram loop or loops of the current echocardiogram examination for the echocardiogram view relevant to the selected detected finding.

11. An echocardiogram reporting method performed using a workstation including a display component and at least one user input component, the echocardiogram reporting method comprising:

interfacing with a user via the workstation to enable the user to enter a current report on a current echocardiogram examination of a cardiac subject;

detecting a current finding value in the current report for an echocardiogram finding;

determining a change between the current finding value and a prior finding value for the echocardiogram finding in a prior report on a prior echocardiogram examination of the cardiac subject;

displaying a notification of the change on the display component of the workstation in response to the change satisfying a significance criterion;

in response to the change satisfying the significance criterion, pre-fetching echocardiogram loop or loops of the prior echocardiogram examination for a relevant echocardiogram view via an archival data storage interface;

storing the pre-fetched echocardiogram loop or loops of the prior echocardiogram examination images for the relevant echocardiogram view in storage; and in response to user selection of the notification via the at least one user input component of the workstation, retrieving, via the user selection of the notification via the at least one user input component, the pre-fetched echocardiogram loop or loops of the prior echocardiogram examination images for the relevant echocardiogram view from the storage and then simultaneously displaying echocardiogram loops of the current echocardiogram examination and the retrieved pre-fetched echocardiogram loop or loops of the prior echocardiogram examination for the relevant echocardiogram view that is relevant to the echocardiogram.

12. The echocardiogram reporting method of claim 11 wherein the detecting is performed during the interfacing and detects the current finding value in response to entry of the current finding value in the current report via the interfacing.

13. The echocardiogram reporting method of claim 11 wherein the detecting is triggered by a user selection, during the interfacing, of an option to check the prior report.

14. The echocardiogram reporting method of claim 11 further comprising:

generating a natural language exposition of the change; and incorporating the natural language exposition of the change into the current report.

15. The echocardiogram examination reporting method of claim 11 wherein the loops of images are labeled by view, further comprising identifying loops of images of the relevant view by reading view identification metadata tagged to the loops.

16. A non-transitory storage medium with computer readable instructions, which, when executed by a processor, cause the processor to:

interface with a user to enable the user to enter a current report on a current echocardiogram examination of a cardiac subject;

detect a current finding value in the current report for an echocardiogram finding;

determine a change between the current finding value and a prior finding value for the echocardiogram finding in a prior report on a prior echocardiogram examination of the cardiac subject;

display a notification of the change on the display component of the workstation in response to the change satisfying a significance criterion;

in response to the change satisfying the significance criterion, pre-fetch echocardiogram loop or loops of images of the prior echocardiogram examination for a relevant echocardiogram view via an archival data storage interface;

store the pre-fetched echocardiogram loop or loops of the prior echocardiogram examination images for the relevant echocardiogram view in storage; and in response to user selection of the notification via the at least one user input component of the workstation, retrieve, via the user selection of the notification via the at least one user input component, the pre-fetched echocardiogram loop or loops of the prior echocardiogram examination images for the relevant echocardiogram view from the storage and then simultaneously display echocardiogram loops of images of the current echocardiogram examination and the retrieved pre-fetched echocardiogram loop or loops of images of the prior echocardiogram examination for the relevant echocardiogram view that is relevant to the echocardiogram finding.

17. The non-transitory storage medium of claim 16, wherein the detecting is performed during the interfacing and detects the current finding value in response to entry of the current finding value in the current report via the interfacing.

18. The non-transitory storage medium of claim 16, wherein the detecting is triggered by user selection, during the interfacing, of an option to check the prior report.

19. The non-transitory storage medium of claim 16, wherein the instructions further cause the processor to:

generate a natural language exposition of the change; and incorporate the natural language exposition of the change into the current report.

* * * * *